US008978480B2

(12) United States Patent
Michopoulos et al.

(10) Patent No.: US 8,978,480 B2
(45) Date of Patent: Mar. 17, 2015

(54) RECURSIVE HEXAPOD SYSTEM AND METHOD FOR MULTIAXIAL MECHANICAL TESTING

(75) Inventors: John G. Michopoulos, Washington, DC (US); John C. Hermanson, Madison, WI (US); Athanasios Iliopoulos, Chevy Chase, MD (US)

(73) Assignees: The United States of America, as represented by the Secretary of the Navy, Washington, DC (US); The United States of America as represented by the Secretary of Agriculture, Washington, DC (US)

( * ) Notice: Subject to any disclaimer, the term of this patent is extended or adjusted under 35 U.S.C. 154(b) by 348 days.

(21) Appl. No.: 13/564,794

(22) Filed: Aug. 2, 2012

(65) Prior Publication Data

US 2013/0055825 A1    Mar. 7, 2013

Related U.S. Application Data

(60) Provisional application No. 61/514,092, filed on Aug. 2, 2011.

(51) Int. Cl.
*G01N 3/02* (2006.01)
*G01N 3/08* (2006.01)

(52) U.S. Cl.
CPC .......... *G01N 3/08* (2013.01); *G01N 2203/0042* (2013.01); *G01N 2203/0208* (2013.01); *G01N 2203/0258* (2013.01); *G01N 2203/0617* (2013.01)
USPC ........................................................ 73/857

(58) Field of Classification Search
CPC ............ G01N 3/08; G01N 2203/0042; G01N 2203/0617; G01N 2203/0258; G01N 2203/0208

USPC ............................................ 73/857, 856, 760
See application file for complete search history.

(56) References Cited

U.S. PATENT DOCUMENTS 5,948,994 A * 9/1999 Jen et al. ......................... 73/856
8,214,080 B2 * 7/2012 Petterson ....................... 700/245
(Continued)

OTHER PUBLICATIONS

R. Badaliance et al., "Effects of Computational Technology on Composite Materials Research: The Case of Dissipated Energy Density", presented at the First Hellenic Conference on Composite Materials Research, Xanthi, Greece, Jul. 2-5, 1997, pp. 1-39.

(Continued)

*Primary Examiner* — Lisa Caputo
*Assistant Examiner* — Philip Cotey
(74) *Attorney, Agent, or Firm* — US Naval Research Laboratory; Sally A. Ferrett

(57) ABSTRACT

A recursive hexapod testing machine for mechanical testing of deformable material specimens under six degrees of freedom multiaxial loading. The machine includes a fixed base, a movable base connected to the fixed base at by a hexapod arrangement of six linearly extendable actuator linkages, with an end of each linkages attached to the movable base and the other end of the linkage attached to the fixed base. Each actuator linkage includes a hydraulic cylinder and piston, a digitally-controlled electro-hydraulic servo-valve for actuating the hydraulic cylinder in response to a digital command string, a load cell in line between the piston and the universal joint attached to the movable base, a linear variable displacement transducer for measuring extension of the piston, and a magneto-resistive position transducer for measuring a position of the piston. The servo-valves extend each hydraulic cylinder a predetermined amount to effect a desired motion of the material specimen.

16 Claims, 11 Drawing Sheets

(56) References Cited

U.S. PATENT DOCUMENTS

2006/0164076 A1* 7/2006 Hinz et al. .............. 324/207.21
2010/0310128 A1  12/2010 Iliopoulos et al.
2011/0032090 A1* 2/2011 Provancher ............... 340/407.1
2011/0314935 A1* 12/2011 Krippner et al. ......... 73/862.045

OTHER PUBLICATIONS

J.M. Michopoulos et al., "Toward a Recursive Hexapod for the Multidimensional Mechanical Testing of Composites", Proceedings of the ASME 2010 International Design Engineering Technical Conferences & Computers and Information in Engineering Conference IDETC/CIE 2010, conference date Aug. 15-18, 2010, pp. 1-9.

J.M. Michopoulos et al., Towards the robotic characterization of the constitutive response of composite materials, Composite Structures, vol. 86, pp. 154-164, 2008, (available online Mar. 13, 2008).

J.M. Michopoulos et al., "First Industrial Strength Multi-axial Robotic Testing Campaign for Composite Material Characterization", Proceedings of the ASME 2012 International Design Engineering Technical Conferences & Computers and Information in Engineering Conference IDETC/CIE 2012, conference date Aug. 12-15, 2012, pp. 1-11.

* cited by examiner

STIFF HEXAPOD

COMPLIANT HEXAPODS

| | |
|---|---|
| Ⓢ | SPECIMEN |
| $C_1$ | GRIP LVDTS |
| $C_2$ | ACTUATOR LVDTS |
| $C_3$ | ACTUATOR MAGNETO-RESISTIVE POSITION TRANSDUCER |
| $S_1$ | BASE LOAD CELL |
| $S_2$ | ACTUATOR HYDRAULIC FLUID |
| $S_3$ | ACTUATOR LOAD CELLS |

FIG. 10D $\varepsilon_{xx}$

FIG. 10E $\varepsilon_{yy}$

FIG. 10F $\varepsilon_{xy}$

RECURSIVE HEXAPOD SYSTEM AND METHOD FOR MULTIAXIAL MECHANICAL TESTING

CROSS-REFERENCE TO RELATED APPLICATIONS

This application is a non-provisional under 35 USC 119(e) of, and claims the benefit of, U.S. Provisional Application 61/514,092 filed on Aug. 2, 2011, the entire disclosure of which is incorporated herein in its entirety.

BACKGROUND OF THE INVENTION

1. Technical Field

This application is related to multiaxial testing machinery, methods, and systems for materials testing and characterization, and more particularly to systems for determining reaction forces and displacement behavior under multiaxial tests.

2. Related Technology

Early development of six degree-of-freedom (DoF) mechatronic technology as it evolved as the core technology behind a systematically automated methodology for identifying the constitutive behavior of composites is described in J. G. Michopoulos, J. C. Hermanson, A. Iliopoulos, "Toward a Recursive Hexapod for the Multidimensional Mechanical Testing of Composites, Proc. ASME International Design Engineering Technical Conferences & Computers and Information in Engineering Conference IDETC/CIE 2010, held 15-18 Aug. 2010.

Three dimensional hexapod materials testing machines developed by the Naval Research Laboratory and the USDA Forest Products Laboratory are also described in J. G. Michopoulos, J. C. Hermanson, and T. Furukawa, "Towards the robotic characterization of the constitutive response of composite materials", Composite Structures, Vol. 86, pp. 154-164, 2008.

BRIEF SUMMARY

A materials testing machine for testing materials specimens under multiaxial conditions held between a fixed base and a movable base. The machine includes a fixed base; a movable base, the movable base being connected to the fixed base by a hexapod arrangement of six linearly extendable actuator linkages, a first end of each actuator linkage being attached to the movable base, a second end of each actuator linkage being attached to the fixed base, each of the actuator linkages including a hydraulic cylinder and piston, a digitally controlled electro-hydraulic servo-valve for actuating the hydraulic cylinder in response to a digital command string, a load cell in line between the piston and the universal joint attached to the movable base, and a linear displacement transducer for measuring an extension of the piston, and a magneto-resistive position transducer for measuring a position of the piston. Operation of each of the servo-valves extends each hydraulic cylinder a predetermined amount to effect a desired motion of the material specimen. The positions measured by the six magneto-restrictive displacement transducers are used by controllers for the electro-hydraulic servo-valves for closed loop control of actuator position.

The first end of each actuator linkage can be attached to the movable base with a universal joint, and the second end of each actuator linkage can be attached to the fixed base with a universal joint.

The materials testing machine can also include a gripping fixture for holding a material specimen, the fixture including a lower grip portion fixedly attached to a rigid fixture base, the fixture further including an upper grip, the upper grip and lower grip positioned to hold the material specimen during testing. The fixture base can be connected to the fixed base by a hexapod arrangement of six rigid frame support members, with each frame support member having a load cell positioned to measure the deformation or strain in the frame support. The load cells in the frame support members can be strain-gauge based load cells and the load cells in the actuator linkages can be charge-controlled piezoelectric load cells.

Two pairs of digital video cameras can also be positioned to image the material specimen during testing, with each pair being attached to the fixture base.

The materials testing machine can also include a rigid adapter piece affixed to the movable frame and to the upper grip, or a plurality of rigid adapter pieces of varying heights to accommodate different specimen lengths within the same overall machine height. The rigid adapter piece is formed of a length of a double I-beam, and with the flanges of the double I-beam positioned to be affixed to the movable base and to the upper grip.

The materials testing machine can also include a hexapod arrangement of six extendable linkages between a base for the upper grip and the fixture base, each of the extendable linkages including a linear displacement transducer for measuring the position of the base for the upper grip with respect to the position of the fixture base.

BRIEF DESCRIPTION OF THE DRAWINGS

FIGS. 10B and 10C show the $u_x$ and $u_y$ displacement distributions corresponding to a load increment before failure of the specimen in FIG. 10A, as displayed on a computer display that is part of an exemplary recursive hexapod material testing system.

FIGS. 10D, 10E, and 10F show corresponding distributions of the fields associated with the three in-plane components of strain, $\epsilon_{xx}$, $\epsilon_{yy}$, $\epsilon_{xy}$, respectively, displayed on a computer display that is part of an exemplary recursive hexapod material testing system.

DETAILED DESCRIPTION OF EMBODIMENTS OF THE INVENTION

A mechatronic recursive hexapod for anisotropic materials testing and characterization is described below. The system is intended to fulfill several design goals, including: the system should be reconfigurable and modular; the system should be able to apply the widest possible combination of three translations and three rotations about a frame of reference attached at the center of the specimen as defined by the intersection of its three symmetry planes; the stiffness of the system should be very high and should not allow significant storage of deformation energy; the system should have very low hysteresis, particularly due to joint friction; the displacement resolution should be fine enough to support deformation measurements of stiff material systems; the displacement range in each direction should be large enough to capture the full range of the material loading path; the force range capacity in each actuator direction should be large enough to bring the specimen to "failure" but have enough resolution to capture the incipient behavior at small displacements; single axis displacement and force transducers should be reducible to the 6-DoF displacement and force-moment measurement capability; there should be at least two sets of displacement transducers and two set of force measurement transducers at different stages for redundancy purposes as well as for establishing how much energy is stored and lost in the system; the system should be able to be configured with various set of grips that accommodate the geometry of the specimen while imposing fixed boundary conditions without damaging the specimen; and a subsystem should be able to measure the full field displacement and strain from both sides of the specimen.

Figure 1:
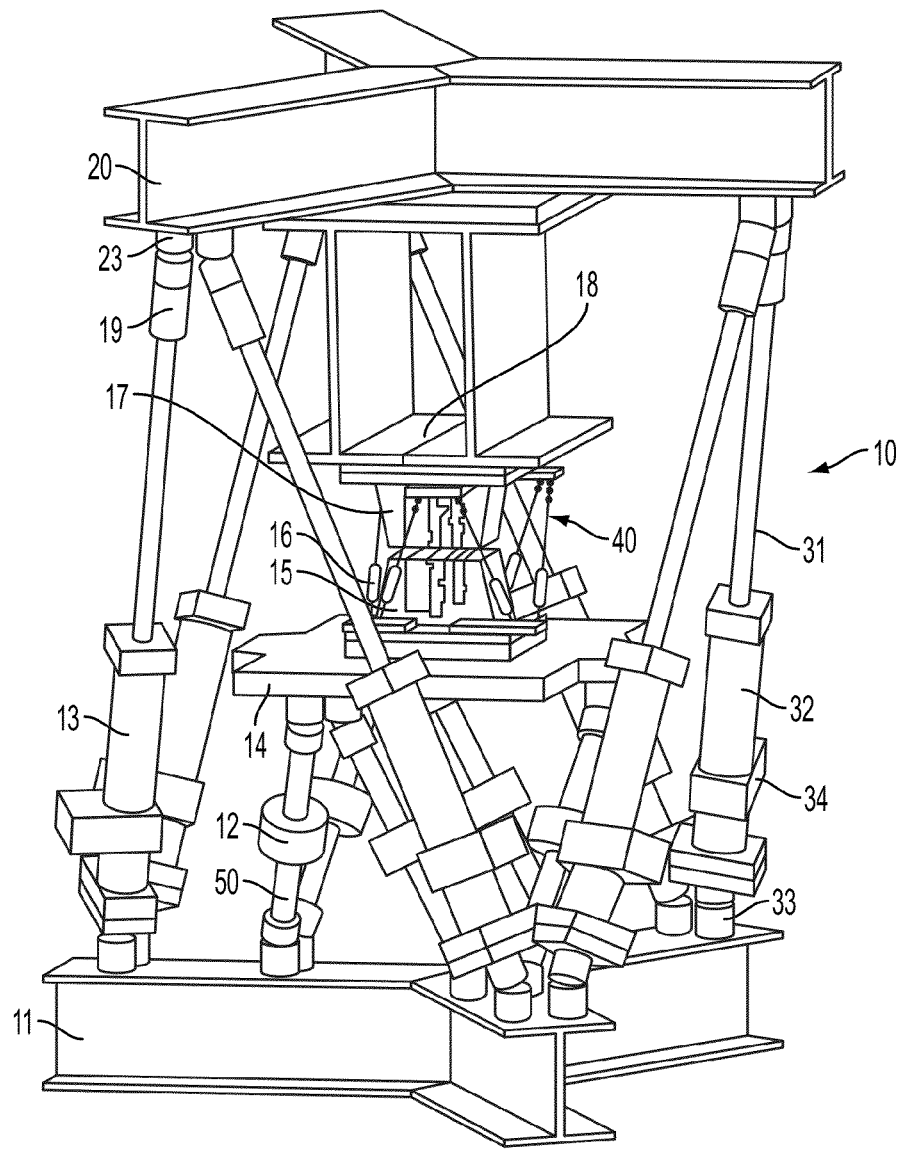
FIG. 1 illustrates an exemplary embodiment of an electromechanical three dimensional recursive hexapod material testing system.
Figure 2:
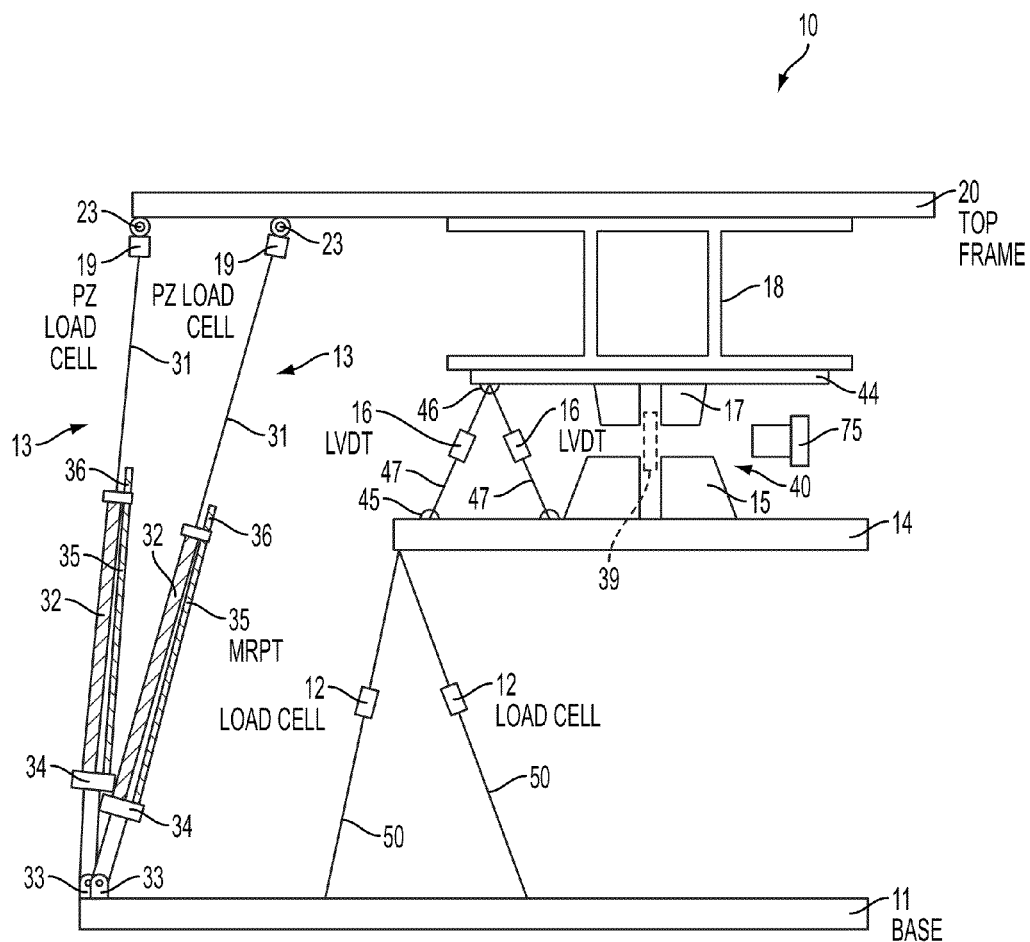
FIG. 2 illustrates another schematic view of the recursive hexapod material testing system of FIG. 1, showing one of each pair of actuators and sensor, together with one of the cameras.

FIG. 1 illustrates an exemplary embodiment of a mechatronic six dimensional recursive hexapod material testing system 10. FIG. 2 illustrates a partial schematic view of the hexapod, showing one of each pair of actuators and sensors, together with one of the cameras.

The fixed base frame 11 can be formed of three rigid legs, joined at a center point, with a three-legged star-shaped configuration, with the angle between any two adjacent legs being approximately 120 degrees. The top frame 20 is a replica of the base, rotated 60 degrees about a vertical axis of symmetry through the hexapod by a movable hydraulic-controlled linkage system, so the top frame 20 is movable in three dimensions with respect to the base frame 11. In this example, the base frame and top frame legs are each formed of three steel I-beams welded at the center point of the base frame 11 and the top frame 20.

Figure 3:
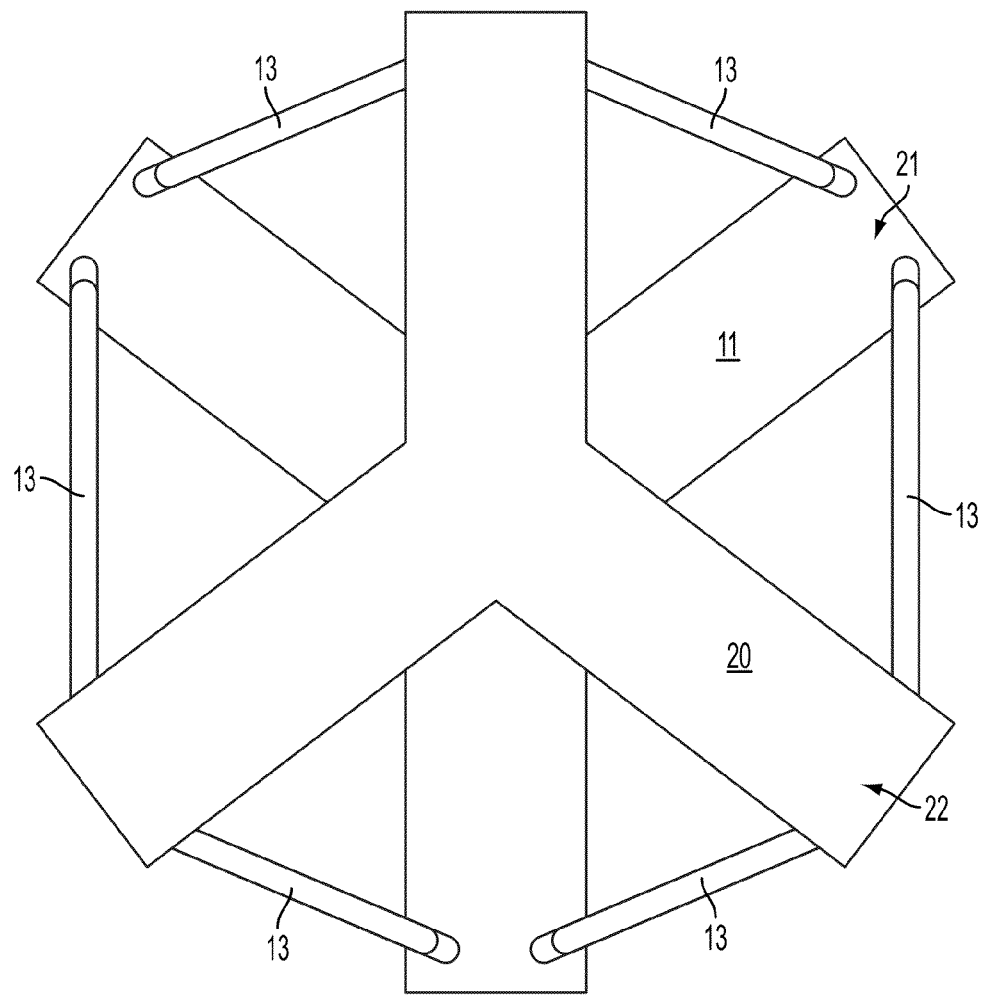
FIG. 3 illustrates the geometry of the recursive hexapod material testing system with a view from above the top movable frame.

FIG. 3 illustrates the geometry of the hexapod 10 with a view from above the top movable frame 20. The structure between the frames has been excluded from this figure for clarity. Attachment points 21, 22 are located at or near the outer end of each of the three legs of the base frame 11 and the top frame 20. Six extendable actuators 13 connect the top frame and base frame, and each actuator is connected to the top frame and the base frame at the attachment point. Universal joints 23, 33, are positioned at each end of the actuator 13 and connect each actuator 13 to the top frame 20 and the base frame 11 at the attachment point. The linkages 13 are arranged so that each of the top frame attachment points is connected by two linkages 13 to the two adjacent base frame attachment points on the base 11.

Figure 4:
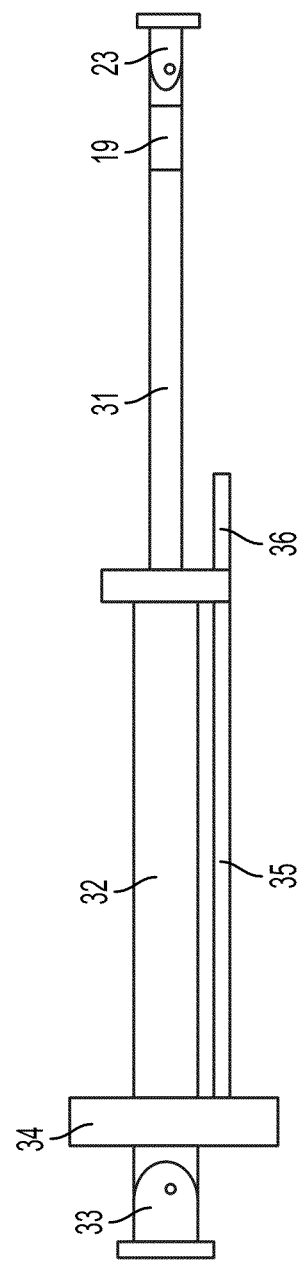
FIG. 4 illustrates the actuators between the base frame and the top frame of the recursive hexapod material testing system of FIG. 1 in more detail.

FIG. 4 illustrates the actuators 13 in more detail. Each actuator includes a hydraulic cylinder 32, a piston rod 31, and an electro-hydraulic servo-valve 34 for controlling the hydraulic cylinder. Two position sensors measure the extension of the piston rod, including a magneto-restrictive position transducer 35 and a linear displacement transducer 36 arranged parallel to the hydraulic cylinder 32 and piston rod 31 for measuring the extension of the piston rod 31. In an exemplary embodiment, the linear displacement transducers are DC LVDTs (DC-operated linear variable differential transducers).

The base 11, the movable frame 20, and the six linkage actuators 13 define a first hexapod recursion. As will be discussed in later paragraphs, five additional hexapod recursions are formed between different elements of the system. By controlling the length of the linkages through actuation of the hydraulic cylinder 32, the six degree of freedom pose of the top frame 20 is controlled kinematically. Extension or retraction of each of the extendable linkage actuators 13 is independently controlled, so the top frame 20 can be moved in any direction with respect to the base frame 11. This motion allows one end of a vertically held test specimen to be moved in six dimensions: in tension or compression along x, y, z axes, and subject to rotation about a vertical z axis and to bending around the x and y axes.

FIGS. 1 and 2 show the fixture 40 for holding the test specimens positioned between the fixed base 11 and the movable top base 20. The fixture 40 is attached to a lower rigid frame 14, which is connected to the fixed base 11 by a second hexapod support structure. The second hexapod support structure includes six rigid support rods 50, each of which extends between a leg of the base 11 and the fixture's rigid frame 14 in a hexapod configuration. Two of the six rigid support rods are affixed to each of the legs of the base 11, at a location approximately midway along the distance from the center of the base to the end of the leg of the base 11. Each of the six rigid frame support rods 50 has a load cell 12 positioned to measure the deformation or strain in the frame support. In an exemplary embodiment, the support rods 50 are steel and the load-cells 12 are strain gauge-based (SG) load-cells, with a capacity of about 89 kN (20,000 lbf). The hexapod arrangement of rigid support rods 50 and load cells 12 arranged between the base 11 and the fixture's frame 14 constitutes the third recursion.

Referring again to FIG. 2, the actuator 13 also includes load cell 19 near the end of the hydraulic piston 31 close to the top movable frame 20 and the upper universal joint 23. In an exemplary embodiment, the load cells 19 are charge controlled piezoelectric load-cells with a capacity of 220 kN (50,000 lbf) in tension and 130 kN (30,000 lbf) in compression. The servo-valve 34 has an embedded valve controller with an analog-to-digital converter for communication with the external computer. The six load cells 19 arranged at the end of the hydraulic piston rods 31 of the actuator linkages 13 form the second recursion.

As mentioned above, the fixture 40 for specimens is affixed to a lower rigid frame 14, which is connected to the system base 11 by a hexapod arrangement of rigid support rods. As shown in FIGS. 1 and 2, the fixture 40 is also rigidly attached to the movable top frame 20 by a rigid adapter 18. In an exemplary embodiment, the adapter is also known as a double I-beam adapter, as it can be formed of a cross section of a steel double I-beam having top and bottom steel plates and upright steel plates between the top and bottom steel plates. The top steel plate of the I-beam adapter 18 can be rigidly mounted or affixed to the upper frame 20 and the lower steel plate provides an attachment point for the fixture 40. Varying the height of the web of the I-beam enables controlling the separation between the two grips, thus enabling testing specimens of drastically different sizes.

Figure 5:
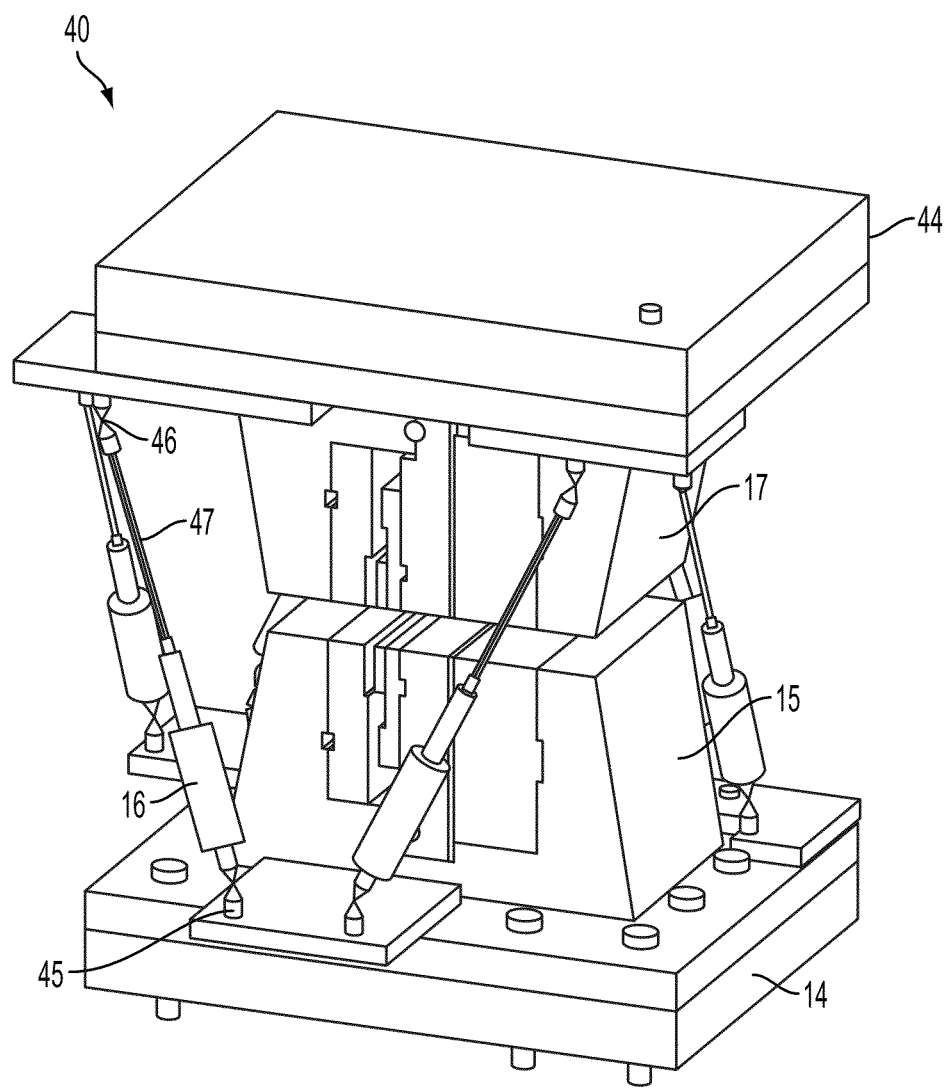
FIG. 5 illustrates the fixture for holding test specimens in the recursive hexapod material testing system of FIG. 1 in more detail.

The fixture 40 is shown in more detail in FIG. 5. The fixture 40 includes an upper grip 17, which is connected to a double I-beam adaptor 18, which is connected to the moving frame 20. Because of the rigid materials and connections, the upper grip 17 is controlled by the motion of the top frame which is controlled by the motion of the actuators. The role of this adaptor double I-beam is to control the location of the upper grip 17 in order to accommodate a particular range of specimen lengths. The system can accommodate different height double I-beams, in order to test different size specimens. Thus, the system can also include a set of rigid double I-beam adapters of various heights, with each of the adapters being suitable for specimens of a particular length. For example, a shorter specimen would be matched with a taller double I-beam adapter, so the total vertical distance between the fixture's base frame 14 and the movable upper frame 20 in its at rest position remains constant. This allows the rapid reconfiguration of the machine to readily test different specimen sizes, by switching out the double I-beam adapter.

The lower grip 15 is configured to hold the lower part of the specimen, while the upper grip 17 holds the upper part of the specimen.

In operation, the controllers direct the actuators 13 to move the top movable frame 20 according to a pre-programmed profile, and the motion is transmitted to the upper grip 17 by the double I-beam adapter. The specimen is held between the fixed lower grip 15 and the moving upper grip 17. The motions and strains of several locations in the system are measured during the test, as discussed in later paragraphs, and sensors, including cameras, record the physical state of the specimen.

The last three recursions of the hexapod are three sets of linear displacement transducers arranged in extendable linkages between the movable upper base 44 and the fixed lower base 14 of the fixture 40. As shown in FIGS. 2 and 4, six linear displacement transducers 16 are arranged in a hexapod configuration between the upper and lower bases for the fixture 40. In an exemplary embodiment, the linear displacement transducers 16 are AC LVDTs (AC-operated linear variable differential transducers). The six linear displacement transducers 16 measure the change in distance along the linearly extendable linkages 47. The six LVDTs 16 define the six degrees of freedom pose of the upper grip assembly, and form the fourth recursion in the hexapod system.

Universal joints 45, 46, are located at the ends of each of the LVDT linkages 47. These six pairs of universal joints 45, 46 allow movement in six dimensions of the upper grip 17 for holding the upper end of the test specimen.

The set of six linear displacement transducers 36 (DC-LVDTs) that are arranged parallel to the actuating hydraulic cylinders 32 comprise the fifth recursion of the system.

The positions measured by the six magneto-restrictive (MR) displacement transducers 35 are used by the controllers for the hydraulic actuator valves 34 for closed loop control of actuator position. These six magneto-restrictive displacement transducers 35 form the sixth recursion of the hexapod.

Referring again to FIG. 2, it is noted that in an exemplary embodiment in which the rigid support rods 50 that support the fixture frame 14 have equal lengths, the fixture frame is parallel to the base 11, with each preferably being horizontal, and the relative position of the base 11 and the fixture frame 14 will remain essentially constant during specimen testing, with only minor movement of the fixture frame due to applied loads. Similarly, due to the strength and rigidity of the adapter piece 18, the upper frame 44 of the fixture and the top frame 20 of the system will maintain their relative parallel positions with respect to each other even during specimen testing, with only minor movement due to applied loads. This minor flexure and other movement of system components is accounted for by the computer when generating digital control strings for servo-valve control, based on measurements of the component positions with the additional position sensors (two sets of LVDTs 16 and 36) and the two sets of load cells 19 and 12.

A whole field strain measurement subsystem includes a plurality of digital video and/or still cameras positioned facing the specimen, to record images of the specimen during the test. In an exemplary embodiment, four cameras are arranged surrounding the specimen, with two cameras facing each of the two faces of the specimen. Each pair of cameras is held in position on the lower fixture rigid frame 14 by a mounting system (not shown).

Figure 6A:
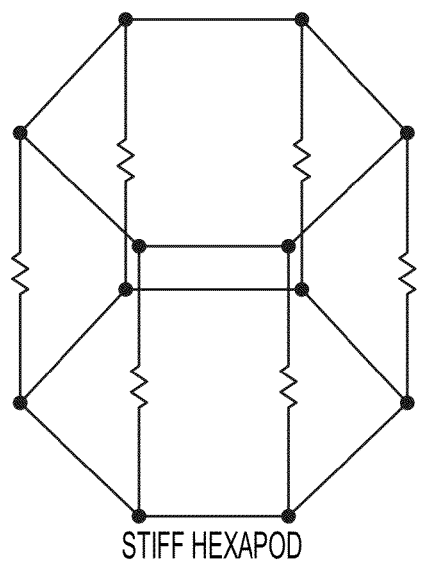
FIGS. 6A and 6B are circuit representations of the compliant and stiff sensors and actuators.
Figure 6B:
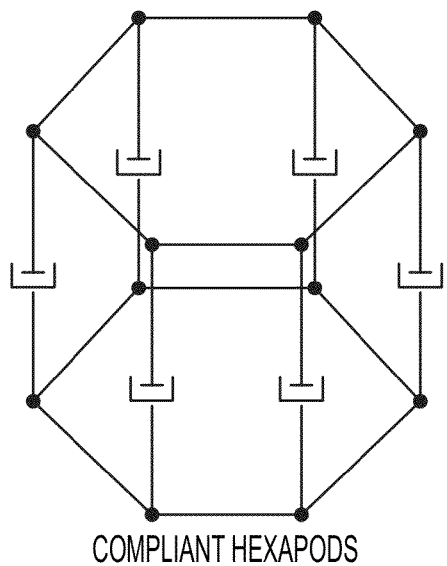
Figure 6C:
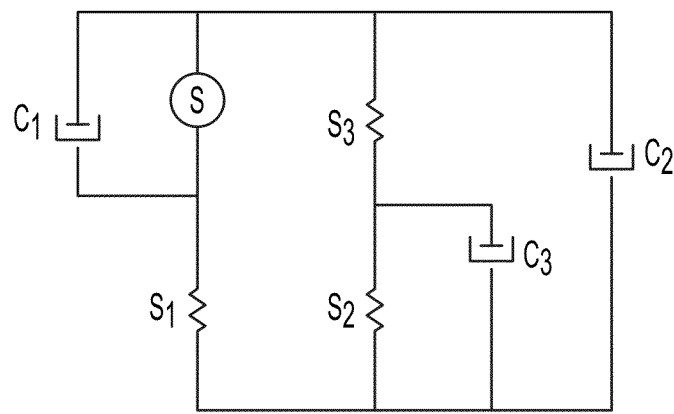
FIG. 6C illustrates a circuit representation all the sensors and actuators.

FIGS. 6A and 6B define a representation syntax for the stiff and compliant sensors in terms of resistance and capacitance or compliance. FIG. 6C is a circuit representation of the actuators and sensors, with (S) representing the specimen, S1 representing the base load cells 12, S2 representing the actuator hydraulic fluid, S3 representing the actuator load cells 19, C1 representing the grip LVDTs 16, C2 representing the actuator LVDTs 36, and C3 representing the actuator magneto-restrictive position sensors 36.

Three of the hexapod recursions are stiff, including the actuators and the two sets of load cells, while the other hexapod recursions are compliant, including the three sets of displacement transducers.

Figure 7:
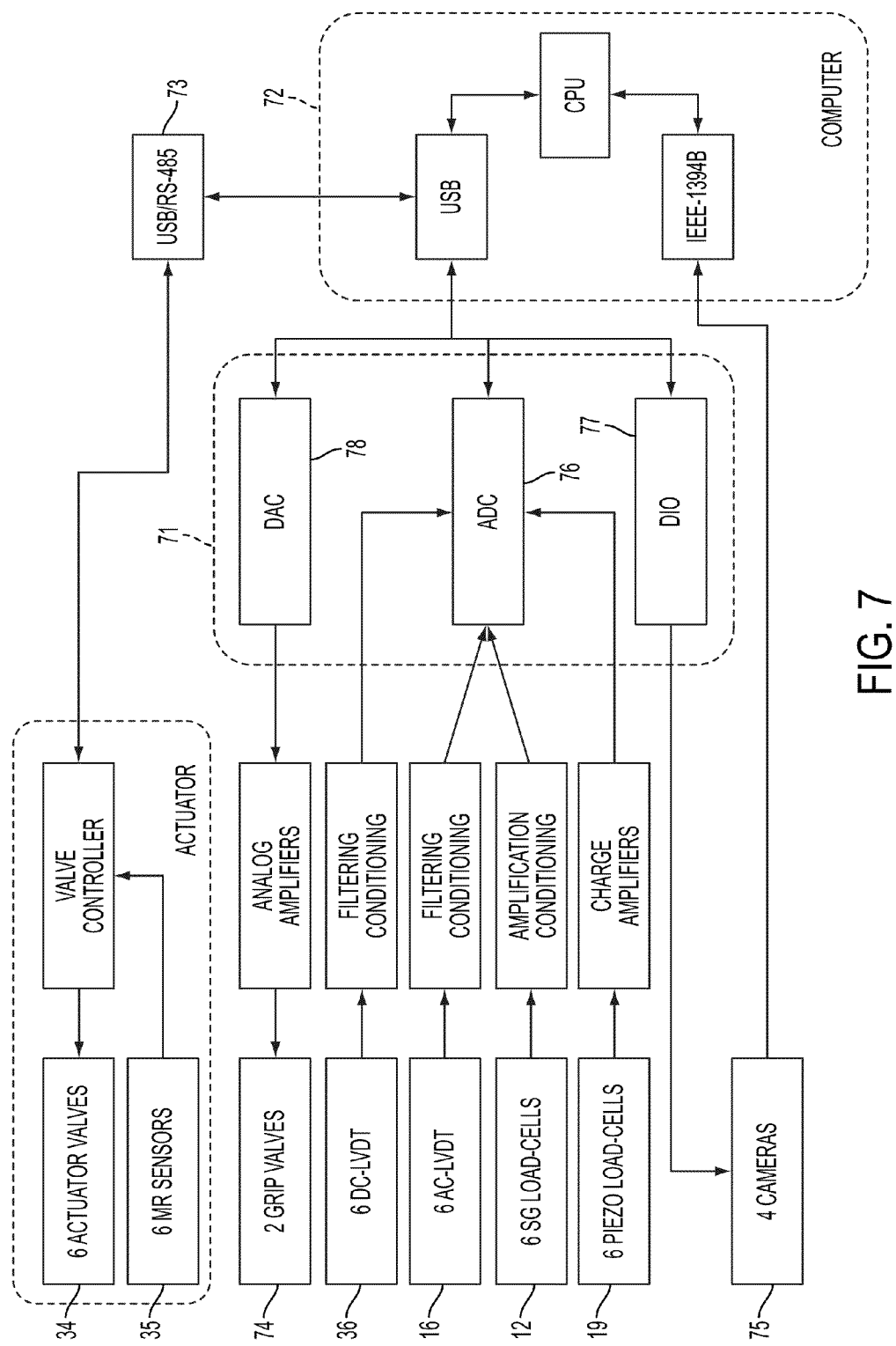
FIG. 7 illustrates the control system architecture for the recursive hexapod material testing system of FIG. 1.

FIG. 7 shows the system 10 from a system control perspective. The column of devices on the left side of FIG. 7 represent all the electromechanical devices attached on the system (actuator valves, magneto-resistive sensors, the two grip valves, six DC-LVDTs, six AC-LVTDs, six SG load cells, six piezoelectric load cells) and the four video cameras used for the whole field strain measurement subsystem. An electronic data acquisition and control device 71 includes the analog-to-digital converter (ADC), the digital-to-analog converter (DAC) and the digital input/output (DIO) devices and can be connected to the USB bus of the controlling computer 71. The data acquisition and control system can be, for example, a data acquisition unit commercially available from National Instruments Corporation, headquartered in Austin, Tex.

In an exemplary embodiment, the positions of the actuators are controlled through the computer via a daisy chained serial bus (RS-485) that communicates to the computer 72 via a RS-485 to USB bus converter 73. A digital string containing the desired position of all actuators is sent from the main controller computer via the bus 73. The servo-valve module 34 contains a built-in DAC that translates the command to a desired position voltage. The embedded controller on the servo-valve compares the target position voltage from the value reported from the magneto-restrictive linear position transducers and sends a current to the solenoid of the servo-valve to open it or close it so the controller can minimize the difference between target and current position, thus causing the piston rod 31 to move as requested. In an exemplary embodiment, the magneto-restrictive linear position transducers 35 are commercially available transducers manufactured by MTS Systems Corporation, under the registered tradename TEMPSONICS, although other devices may also be suitable.

As discussed above, the gripping fixture 40 has an upper grip 17 and lower grip 15 with valves that control the gripping and ungripping motions, to secure and release the ends of a test specimen 39. The DAC 78 sends a voltage to the analog-controlled valves 74 that determine the position of the movable part of the grip assemblies 17 and 15 causing the specimens to be gripped or un-gripped. The ADC 76 converts all the analog voltages produced by the signal conditioning devices originating from the displacement and force transducers to a digital form to be communicated to the controller computer via the USB bus. The video frames from the four cameras 75 are transferred to the computer via 1394-B firewire 800 Mb/s bus. The DIO 77 triggers the video cameras 75 to ensure synchronization with the force and displacement transducers.

In an exemplary embodiment, the recursive hexapod material testing system 10 can also include robotic loading and unloading devices (not shown), controlled by the computer system, for loading test specimens into the fixture, and removing the test specimens after the test is complete. The devices are positioned on either side of the fixture 40, in locations that do not obscure the view of the cameras. Alternatively, the fixture can be manually loaded and unloaded, however, the system's ability to accomplish numerous repetitive tests is expected to be negatively impacted. The robotic loading and unloading systems are preferably integrated into the control subsystem for the material testing system, to ensure loading and unloading of specimens is synchronized with the gripping, test specimen movement, video capture, and ungripping steps.

Data collected by the hexapod material specimen testing device 10 described above can be used in any of several methods of models for characterizing the constitutive response of materials. An aspect of the invention is directed to the method set forth in the following paragraphs.

The first law of thermodynamics can express the energy balance, which forms an objective function that can be minimized by following a global optimization methodology, according to the following form:

$$J = \int_\Omega [W_r(C; \varepsilon) + W_i(D; \varepsilon)] dV - \int_{\Gamma i} t \cdot u \, ds \tag{1}$$

where $W_r$ and $W_i$ are the recoverable and non-recoverable strain energy density functions, t and u are the vectors of the boundary tractions and displacements, $\varepsilon$ is the strain state, and the components of the tensors C and D contain the material parameters to be determined by the optimization procedure. The boundary tractions and displacements and the surface strains are all determined from the sensors of the hexapod system 10 above.

Figure 8B:
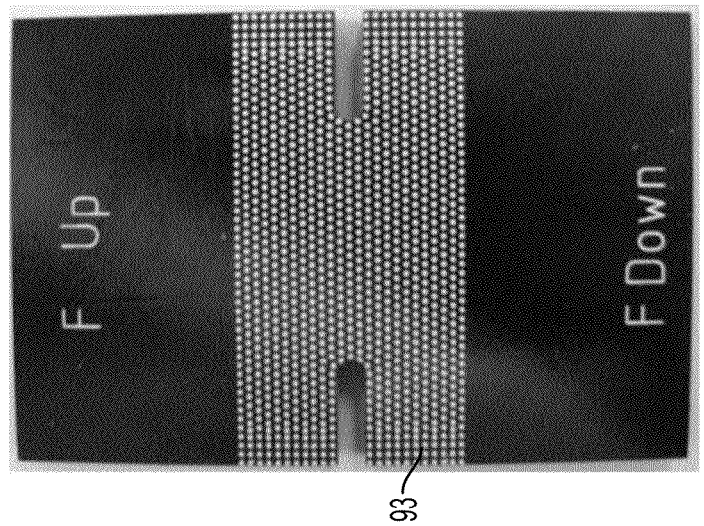
FIG. 8B shows a test specimen with markings for camera displacement measurement during a method of testing a material specimen with the hexapod test system of FIG. 1.
Figure 8A:
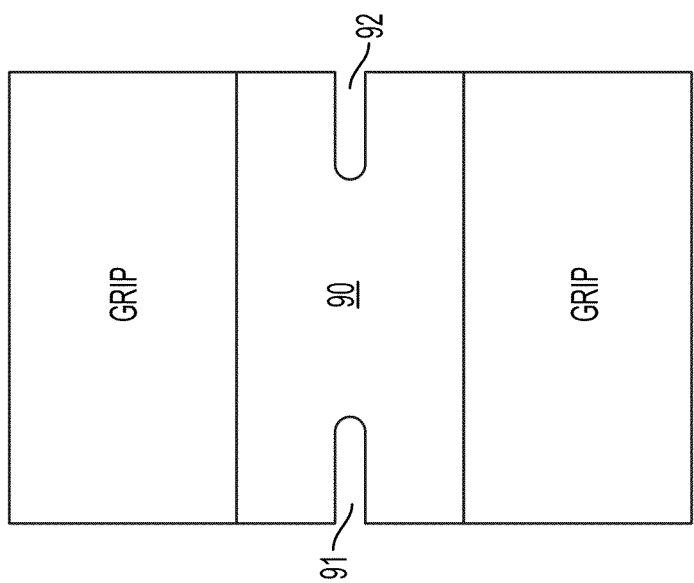
FIG. 8A shows the dimensions of a suitable test specimen for use in the recursive hexapod material testing system of FIG. 1.

FIG. 8A shows a sketch of a typical specimen used for the verification and validation tests of the system. The user is free to define and choose any shape specimen required. The flat material test specimen 90 has its ends placed into grips with the central area free of the grips. The notches 91, 92 on the sides of the specimen are included to disturb the strain field and to ensure that some areas of the specimen (not necessarily near the notch roots) will experience non-linear constitutive response due to the corresponding strain fields. In this example, the thickness of a specimen is approximately 4.16 mm (0.16 inch), the width is 50 mm (2 inches). Approximately 25 mm (1 inch) of the specimen at each end is held by the upper and the lower grips, leaving approximately 25 mm (1 inch) free. Each notch is approximately 3 mm (0.12 inch) wide and extends about 12 mm (0.5 inches) from each side of the specimen.

FIG. 8B shows a test specimen 93 with a number of dots in the central free area, the "deformation domain". The dots are markers that are used to measure the displacement and strain fields during the deformation test. The imaging system photographs the specimen, with the markers, and based on the motion of the markers, the displacement and strain fields are determined according to a two-dimensional or three dimensional mesh free random grid method or another suitable method. Additional information is as described in Iliopoulos, A., Michopoulos, J., and Andrianopoulos, N., "Performance sensitivity analysis of the mesh-free random grid method for whole field strain measurements", 2008 ASME International Design Engineering Technical Conferences and Computers and Information in Engineering Conference, DETC 2008, Vol. 3, pp. 545-555; Iliopoulos, A., and Michopoulos, J. G., "Effects of anisotropy on the performance sensitivity of the meshfree random grid method for whole field strain measurement", Proceedings of the ASME 2009 International Design Engineering Technical Conferences & Computers and Information in Engineering Conference IDETC/CIE 2009, ASME, ed., no. DETC2009/CIE-86962; and Michopoulos, J. G., and Iliopoulos, A., "A computational workbench for remote full field 2d displacement and strain measurements", Proceedings of the ASME 2009 International Design Engineering Technical Conferences & Computers and Information in Engineering Conference IDETC/CIE 2009, ASME, ed., no. DETC2009/CIE-86900; and in patent application Ser. No. 12/793,594, published as U.S. Patent Application Publication No. 2010-0310128, each of which is incorporated herein in its entirety. Three dimensional displacement can be found using the methods described in Michopoulos, J. G. and Iliopoulos, A., "A computational workbench for remote full field 3D displacement and strain measurements", Proceedings of the ASME 2011 International Design Engineering Technical Conferences & Computers and Information in Engineering Conference IDETC/CIE 2011, ASME, ed., no. DETC2011/CIE-47739, and in provisional patent application 61/514,083, filed on Aug. 2, 2011, each of which is incorporated herein in its entirety.

The mission of the system is to be programmed to follow loading paths and measure boundary displacements and reaction forces and moments resulting from the mechanical response of the specimens under testing.

Here, the reaction forces are measured by the load cells 19 and 12, and the displacements are measured by the position transducers 35, 36, and 16 of the recursive hexapod materials test machine 10.

The 6D load space can be sampled by commanding the hexapod system to follow radial proportional paths and acquire data at the points that these paths intersect concentric spheres. The term proportional path here means that every path i when represented as a vector starting in the origin and ending at point j, can be resolved to its components in the 6-D frame $(u_x; u_y; u_z; r_x; r_y; r_z)$ according to the equation $$p_i^j = p_{i1}^j u_x + p_{i2}^j u_y + p_{i3}^j u_z + p_{i4}^j u_{rx} + p_{i5}^j u_{ry} + p_{i6}^j u_{rz} \tag{2}$$

where the p terms ($p_{i1}^j u_x$ etc.) in equation (2) are the magnitudes of each of the components.

Each path p represents the planned amount of movement of the end of the specimen in the six dimensions: x, y, z, and rotation and bending around the x and y axes to be accomplished during a particular test.

Equation (2) can also be written as $$p_i^j = r_i^j a_{ik}^j, \text{ with } k \in \{1,2,3,4,5,6\}, \text{ and with } a_{ik}^j = a_{ik}^{j+1} \quad (3)$$

A convenient parameterization of the loading paths can be obtained by invoking a transformation from hyperspherical to Cartesian frame of reference as follows:

$$p_{i,1}^j = r_i^j \cos(\phi_1^i)$$

$$p_{i,2}^j = r_i^j \sin(\phi_1^i)\cos(\phi_1^i)$$

$$p_{i,3}^j = r_i^j \sin(\phi_1^i)\sin(\phi_2^i)\cos(\phi_2^i)$$

$$p_{i,4}^j = r_i^j \sin(\phi_1^i)\sin(\phi_2^i)\sin(\phi_3^i)\cos(\phi_3^i)$$

$$p_{i,5}^j = r_i^j \sin(\phi_1^i)\sin(\phi_2^i)\sin(\phi_3^i)\sin(\phi_4^i)\cos(\phi_4^i)$$

$$p_{i,6}^j = r_i^j \sin(\phi_1^i)\sin(\phi_2^i)\sin(\phi_3^i)\sin(\phi_4^i)\sin(\phi_5^i)\cos(\phi_5^i) \quad (4)$$

where $r_i^j$ and $\phi_i^j$ are the magnitude of the path and the angles between the path and the planes defined by the basis vectors of the 6D kinematic space.

It is often desired to minimize the number of test specimens that is needed to characterize a material system, to decrease costs and shorten test time. Using one specimen per path has yielded good results. For each type of material to be tested, it is suitable to use at least as many specimens as the number of paths used to sample the excitation space. In an exemplary embodiment, it is suitable to use twice as many specimens as the number of paths, with each path being tested twice.

The number of paths $n_{paths}$ can be written as a function of the dimension n of the space, as follows:

$$n_{paths} = (4+nep) + (1+2nep)^{n-2}, \quad (5)$$

with the number of equatorial points nep as discussed in Michopoulos, J., Hermanson, J., Furukawa, T., "Towards the Robotic Identification of Constitutive Response of Composite Materials", J. of Composite Structures, Vol. 86, pp. 154-164 (2008).

An intermediate scenario (in terms of required number of specimens) could be based on the fact that the rotation components generate motion on the plane they are normal to. Thus, only four out of the six components can be linearly independent. In this case n=4 and nep=1, equation (5) generates 72 paths. This seems to promote the solution of utilizing one of the fifteen 4-D subspaces that can be used for defining the loading paths. A computationally intensive methodology for determining the best subspace among the fifteen is presented in Iliopoulos, A., et al., "Loading subspace selection for multidimensional characterization tests via computational experiments", Proceedings of the ASME 2010 International Design Engineering Technical Conferences & Computers and Information in Engineering Conference IDETC/CIE 2010, ASME, ed., no. DETC2010/CIE-28741, the entire disclosure of which is incorporated herein in its entirety.

A computer processor can implement instructions for controlling the actuators, controlling the cameras, storing the imagery, and storing the hexapod position information associated with each specimen at a series of times during the test. The computer processor can also receive instructions from the user via a graphical user interface, and can transmit signals to a display device to illustrate test progress, and the strain components at each location on the specimen over the test period. In an exemplary embodiment, the main control loop and the entire associated loop for the testing composite material specimens for their characterization is implemented on LabVIEW, because of the ease of prototyping and the availability of device drivers for most DAC and ADC devices that are available on the market today.

Figure 9:
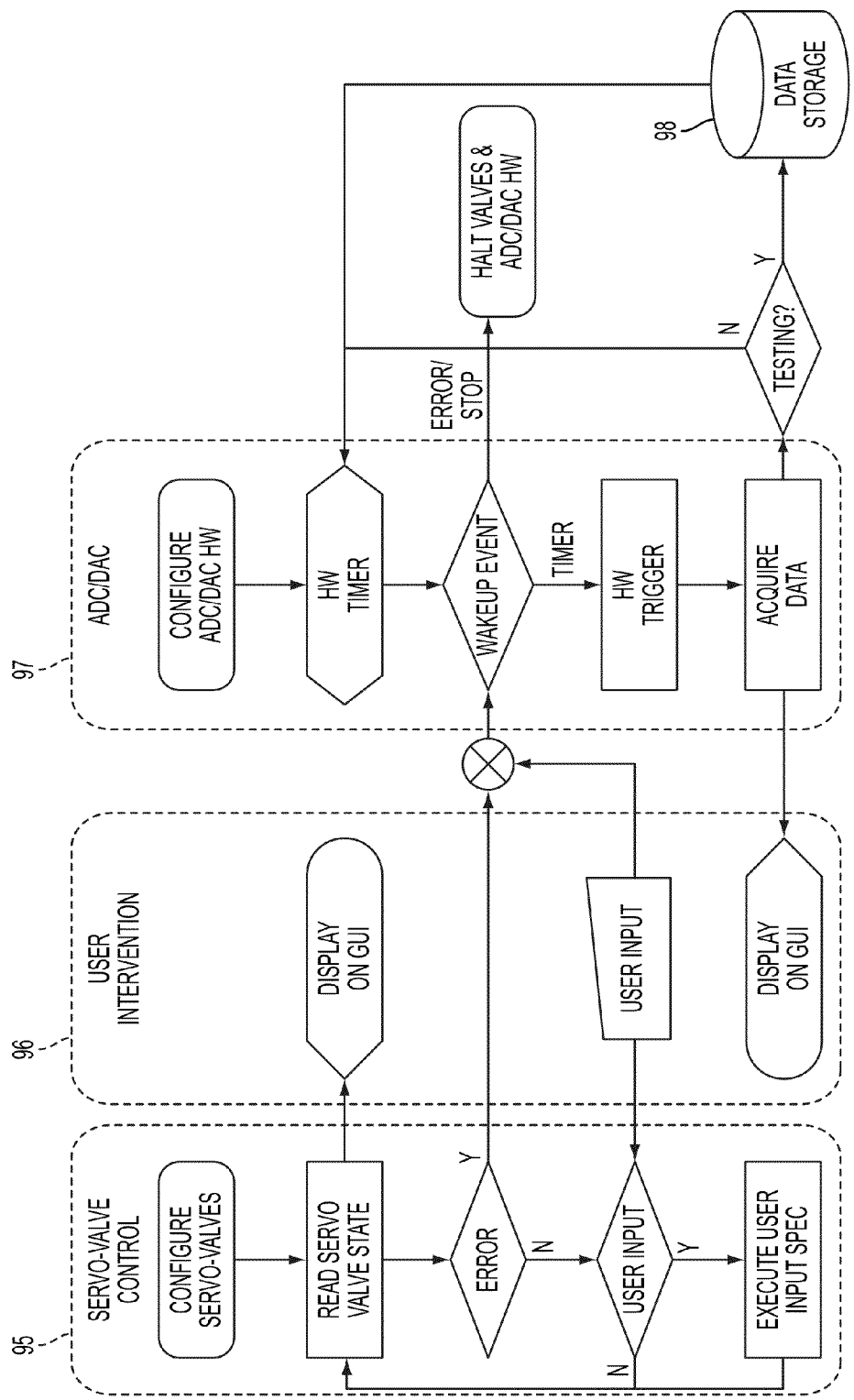
FIG. 9 shows the software logic for the recursive hexapod material testing system of FIG. 1.

The overview of the logic implemented by the software designed for controlling the system is shown in FIG. 9. The diagram shows the servo-valve control subsystem 95, the user intervention unit 96, the ADC/DAC subsystems 97, and the data handling subsystem 98. Generally, the implementation is formulated both under the dataflow and event-driven programming paradigms and essentially begins with the initialization of the configuration operations of the valves and the ADC/DAC hardware. The LabVIEW implementation of this logic can constitute the control software for the entire system.

Figure 10A:
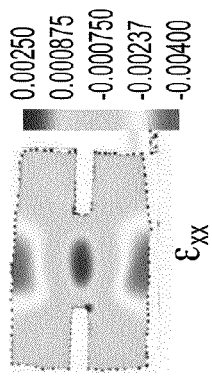
FIG. 10A shows an image taken of a carbon-epoxy specimen mounted between the grips after specimen failure, by a camera of the recursive hexapod material testing system of FIG. 1.
Figure 10A:
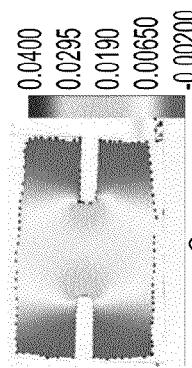
Figure 10A:
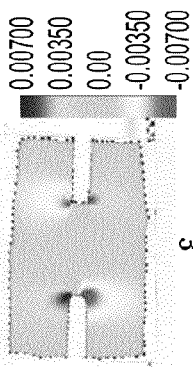
Figure 10A:
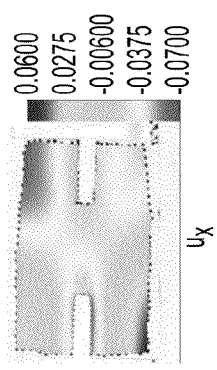
Figure 10A:
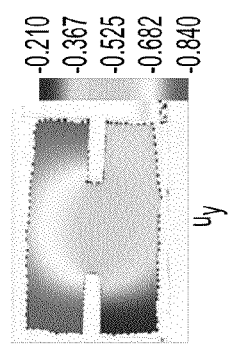
Figure 10A:
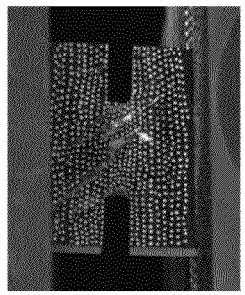

FIG. 10A shows a carbon-epoxy specimen mounted between the grips, with the photograph being taken after specimen failure.

The system status and test results are graphically shown on a display connected to the computer 71. For example, FIGS. 10B and 10C are typical of a screen display showing the $u_x$ and $u_y$ displacement distributions corresponding to a load increment before failure are shown. The applied loading path was mostly tension. FIGS. 10D, 10E, and 10F are typical of a screen display showing corresponding distributions of the fields associated with the three in-plane components of strain, $\epsilon_{xx}$, $\epsilon_{yy}$, $\epsilon_{xy}$, respectively.

The system described herein has advantages compared to previous material testing systems. As one example, the system allows precise control of the specimen's path and loading profile through digital control of the actuator control valves. As another example, the four cameras allow three dimensional determination of displacement and strain using the three dimensional REMDIS system with randomly marked specimens. Further, the system is programmed to rapidly and precisely load, grip, move and release the specimens, with each specimen being subjected to a different pre-programmed six dimensional movement path. The three hexapod arrangements of load cells, LVDTs, and MR position transducers in each actuator leg provide precise position information for the actuators. The hexapod arrangement of linear variable transducers in the specimen fixture further measures the position of the upper fixture grip with respect to the lower grips, allowing further refinement of the actuator control signals by the computer program.

The fixed base frame 11 is described in the example above as being formed of three I-beams, however, various materials and configurations may be suitable, as long as the base forms a heavy rigid floor for the system that suitably keeps the fixed components in alignment without moving. In some instances, it may be suitable to consider a component of another structure, such as the floor of a building or a flatbed of a truck, to be the base, and to attach the linkages directly to that structure. Similarly, the movable frame 20 can be formed with different strong and rigid materials or a different shape. The movable frame must be able to maintain the relative positions of the universal joints connected to the linkages, and to hold up the rigid adapter and upper grip of the fixture even under repeated test loads of numerous specimens. Flat steel plates could be used for both the fixed base 11 and the movable frame 20. In such a configuration, the hexapod linkages would be attached in the same triangular pattern shown in FIG. 2. The steel I-beam frame and base, however, provide excellent rigidity and strength.

The system can include the visually patterned test body or test specimen, the hexapod test device for deforming the body, the image acquisition system, data storage for storing the images and associated information, communications links for transmitting the images and associated information to the computer system that implements the processing steps (including the point or pattern matching algorithms, and algorithms for calculating and displaying the full field).

Although the system preferably uses four digital video cameras, it can also be implemented with digital images from a digital camera, or using digital images from digitization of non-digital images, such as, but not limited to, film cameras. The system can be implemented using digital image frames from digital or film video equipment or other motion picture type cameras.

The hexapod materials testing machine 10 is suitable for testing many types of materials and specimens, including isotropic materials and anisotropic materials. It is particularly suitable for testing anisotropic materials, such as laminates, because of its six degrees of freedom. Carbon-graphite epoxy based composite materials are one such anisotropic material envisioned to be tested by the hexapod materials testing machine. The central region of the specimens are typically marked on both sides with painted or applied dots in a random manner discussed in patent application Ser. No. 12/793,594, published as U.S. Patent Application Publication No. 2010-0310128.

Portions of the system operate in a computing operating environment, for example, a desktop computer, a laptop computer, a mobile computer, a server computer, and the like, in which embodiments of the invention may be practiced. A brief, general description of a suitable computing environment in which embodiments of the invention may be implemented. While the invention is described in the general context of program modules that execute in conjunction with program modules that run on an operating system on a personal computer, those skilled in the art will recognize that the invention may also be implemented in combination with other types of computer systems and program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

An illustrative operating environment for embodiments of the invention will be described. A computer comprises a general purpose desktop, laptop, handheld, mobile or other type of computer (computing device) capable of executing one or more application programs. The computer includes at least one central processing unit ("CPU"), a system memory, including a random access memory ("RAM") and a read-only memory ("ROM"), and a system bus that couples the memory to the CPU. A basic input/output system containing the basic routines that help to transfer information between elements within the computer, such as during startup, is stored in the ROM. The computer further includes a mass storage device for storing an operating system, application programs, and other program modules.

The mass storage device is connected to the CPU through a mass storage controller (not shown) connected to the bus. The mass storage device and its associated computer-readable media provide non-volatile storage for the computer. Although the description of computer-readable media contained herein refers to a mass storage device, such as a hard disk or CD-ROM drive, it should be appreciated by those skilled in the art that computer-readable media can be any available media that can be accessed or utilized by the computer.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other tangible non-transitory medium which can be used to store the desired information and which can be accessed by the computer.

According to one embodiment, the computational workbench for visualizing the full field characteristics of deformable bodies may include a number of program modules.

According to various embodiments of the invention, the computer may operate in a networked environment using logical connections to remote computers through a network, such as a local network, the Internet, etc. for example. The computer may connect to the network through a network interface unit connected to the bus. It should be appreciated that the network interface unit may also be utilized to connect to other types of networks and remote computing systems. The computer may also include an input/output controller for receiving and processing input from a number of other devices, including a keyboard, mouse, etc. (not shown). Similarly, an input/output controller may provide output to a display screen, a printer, or other type of output device.

As mentioned briefly above, a number of program modules and data files may be stored in the mass storage device and RAM of the computer, including an operating system suitable for controlling the operation of a networked personal computer. The mass storage device and RAM may also store one or more program modules. In particular, the mass storage device and the RAM may store application programs, such as a software application, for example, a word processing application, a spreadsheet application, a slide presentation application, a database application, etc.

It should be appreciated that various embodiments of the present invention may be implemented as a sequence of computer implemented acts or program modules running on a computing system and/or as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present invention as described herein.

What is claimed as new and desired to be protected by Letters Patent of the United States is:

1. A materials testing machine for six degrees of freedom multiaxial testing of specimens held between a fixed base and a movable base, the machine comprising:
 a fixed base; and
 a movable base, the movable base being connected to the fixed base by a hexapod arrangement of six linearly extendable actuator linkages, a first end of each actuator linkage being attached to the movable base, a second end of each actuator linkage being attached to the fixed base;

each of the actuator linkages including a hydraulic cylinder and piston, a digitally controlled electro-hydraulic servo-valve for actuating the hydraulic cylinder in response to a digital command string, a load cell in line between the piston and a universal joint attached to the movable base, a linear displacement transducer for measuring an extension of the piston, and a magneto-resistive position transducer for measuring a position of the piston, wherein in operation, operation of each of the servo-valves extends each hydraulic cylinder a predetermined amount to effect a desired motion of the material specimen.

2. The materials testing machine according to claim 1, wherein the first end of each actuator linkage is attached to the movable base with a universal joint, and the second end of each actuator linkage is attached to the fixed base with a universal joint.

3. The materials testing machine according to claim 1, wherein in operation, the positions measured by the six magneto-restrictive displacement transducers are used by controllers for the electro-hydraulic servo-valves for closed loop control of actuator position.

4. The materials testing machine according to claim 1, further comprising:

a fixture for holding a material specimen, the fixture including a lower grip portion fixedly attached to a rigid fixture base, the fixture further including an upper grip, the upper grip and lower grip positioned to hold the material specimen during testing, the fixture base being connected to the fixed base by a hexapod arrangement of six rigid frame support members, each frame support member having a load cell positioned to measure the deformation or strain in the frame support.

5. The materials testing machine according to claim 4, wherein the load cells in the frame support members are strain-gauge based load cells and the load cells in the actuator linkages are charge-controlled piezoelectric load cells.

6. The materials testing machine according to claim 4, further comprising:

two pairs of digital video cameras, each pair being attached to the fixture base, each camera positioned to image the material specimen during testing.

7. The materials testing machine according to claim 4, further comprising:

a rigid adapter piece affixed to the movable frame and to the upper grip, allowing testing of a large range of different specimen sizes.

8. The materials testing machine of claim 7, further comprising:

a plurality of rigid adapter pieces of varying heights to accommodate different specimen lengths within the same overall machine height.

9. The materials testing machine according to claim 7, wherein the rigid adapter piece is formed of a length of a double I-beam, and wherein the flanges of the double I-beam are positioned to be affixed to the movable base and to the upper grip.

10. The materials testing machine according to claim 4, further comprising:

a hexapod arrangement of six extendable linkages between a base for the upper grip and the fixture base, each of the extendable linkages including a linear displacement transducer for measuring the position of the base for the upper grip with respect to the position of the fixture base.

11. The materials testing machine according to claim 1, further comprising:

a controller for the electro-hydraulic servo-valve, said controller configured to receive piston position information from the magneto-resistive position transducers and to control said servo-valve based on measured piston position from the magneto-resistive position transducers and on computer-based instructions for a pre-determined path for material specimen loading.

12. The materials testing machine according to claim 11, wherein the controller controls said servo-valve based in part on position information received from the linearly extendable displacement transducers in the actuator linkage, the upper grip position information from the linear displacement transducers in the extendable linkages, and strain or displacement information from the load cells.

13. The materials testing machine according to claim 4, further comprising:

two pairs of digital video cameras, each pair being attached to the fixture base, each camera positioned to image the material specimen during testing.

14. The materials testing machine according to claim 1, wherein the magneto-restrictive displacement transducers are magneto-restrictive linear position transducers.

15. The materials testing machine according to claim 1, wherein the magneto-restrictive linear position transducers measure an extension of the piston.

16. The materials testing machine according to claim 14, wherein operation of each of the servo-valves extends each hydraulic cylinder a predetermined amount to effect a desired motion of the material specimen responsive to piston extension information from the magneto-restrictive linear position transducer.

* * * * *